(12) United States Patent
Hölzl et al.

(10) Patent No.: US 9,644,175 B2
(45) Date of Patent: May 9, 2017

(54) ANTIMICROBIAL AMINO-SALICYLIC ACID DERIVATIVES

(75) Inventors: Werner Hölzl, Eschentzwiller (FR); Janina Purschwitz, Freiburg (DE)

(73) Assignee: BASF SE, Ludwigshafen (DE)

( * ) Notice: Subject to any disclaimer, the term of this patent is extended or adjusted under 35 U.S.C. 154(b) by 442 days.

(21) Appl. No.: 13/391,671

(22) PCT Filed: Aug. 13, 2010

(86) PCT No.: PCT/EP2010/061804
§ 371 (c)(1),
(2), (4) Date: Mar. 27, 2012

(87) PCT Pub. No.: WO2011/023573
PCT Pub. Date: Mar. 3, 2011

(65) Prior Publication Data
US 2012/0189568 A1    Jul. 26, 2012

(30) Foreign Application Priority Data

Aug. 26, 2009  (EP) .................................... 09168669

(51) Int. Cl.
| | | |
|---|---|---|
| *C11D 3/48* | (2006.01) |
| *A61K 8/42* | (2006.01) |
| *A61Q 17/00* | (2006.01) |
| *C11D 3/32* | (2006.01) |
| *A61Q 5/02* | (2006.01) |
| *A61Q 11/02* | (2006.01) |
| *A61Q 15/00* | (2006.01) |

(52) U.S. Cl.
CPC .................. *C11D 3/48* (2013.01); *A61K 8/42* (2013.01); *A61Q 17/005* (2013.01); *C11D 3/32* (2013.01); *A61Q 5/02* (2013.01); *A61Q 11/02* (2013.01); *A61Q 15/00* (2013.01)

(58) Field of Classification Search
CPC .......... A61K 8/42; A61Q 11/02; A61Q 15/00; A61Q 17/005; A61Q 5/02; C11D 3/32; C11D 3/48
See application file for complete search history.

(56) References Cited

U.S. PATENT DOCUMENTS

| | | |
|---|---|---|
| 4,551,279 A | 11/1985 | Mueller et al. |
| 4,933,330 A | 6/1990 | Jorgensen et al. |
| 6,326,364 B1 | 12/2001 | Lin et al. |
| 6,600,063 B1 | 7/2003 | Hearn |
| 2009/0286878 A1 | 11/2009 | Elder |

(Continued)

FOREIGN PATENT DOCUMENTS

| | | | |
|---|---|---|---|
| JP | 57145809 | * 9/1982 | ............. A61K 31/60 |
| WO | 0045803 | 8/2000 | |

OTHER PUBLICATIONS

Lemaire et al. ("Synthesis and Germicidal Activity of Halogenated Salicylanilides and Related Compounds" Journal of Pharmaceutical Sciences, 1961, 50, 831-837).*
JP 57145809 English abstract © 1982 JPO&Japio, p. 1-2.*
Lemaire et al., Journal of Pharmaceutical Sciences, vol. 50, (1961) pp. 831-837.
Taborsky et al., Journal of Pharmaceutical Sciences, vol. 52, No. 6, Jan. 1, 1963, pp. 542-545.
Fischert et al., Biomedical Mass Spectrometry, vol. 11, No. 10, (1984) pp. 539-544.
Chem. Abst. No. 2008:613935 of CN101182298.
Chem. Abst. No. 1983:22273 of JP7145809.
Chem. Abst. No. 1997:340908 of JP9077651.

(Continued)

*Primary Examiner* — Kortney L Klinkel
(74) *Attorney, Agent, or Firm* — Marshall, Gerstein & Borun LLP

(57) ABSTRACT

Disclosed is a novel method for achieving an antimicrobial, preservative and/or microorganism adhesion inhibiting effect, for the protection within an article and/or material or on the surface of an article and/or material. The novel method comprises application of a salicylic compound of the formula (I) wherein one of A and A is a residue of the formula (I'): —NH—CO—$R_1$ while the other is hydrogen; $R_1$ is $C_1$-$C_{22}$alkyl, $C_3$-$C_{12}$cycloalkyl, $C_3$-$C_{12}$cycloalkyl interrupted by O and/or $NR_5$, $C_4$-$C_{12}$aryl, $C_5$-$C_{18}$arylalkyl; $R_2$ is $OR_3$ or $NHR_4$; $R_3$ and $R_4$ are selected from H, $C_1$-$C_{22}$alkyl, $C_3$-$C_{12}$cycloalkyl, $C_3$-$C_{12}$cycloalkyl interrupted by O and/or $NR_5$, $C_4$-$C_{12}$aryl, $C_5$-$C_{18}$arylalkyl; $R_5$ is H or $C_1$-$C_8$alkyl; wherein each aryl moiety is unsubstituted or substituted by $C_1$-$C_4$alkyl, $C_1$-$C_4$alkoxy, $C_1$-$C_4$acyl, $C_1$-$C_4$acyloxy, $C_1$-$C_4$acylamino, $CF_3$, OH, amino, halogen; or an adduct or salt thereof; to said article and/or material.

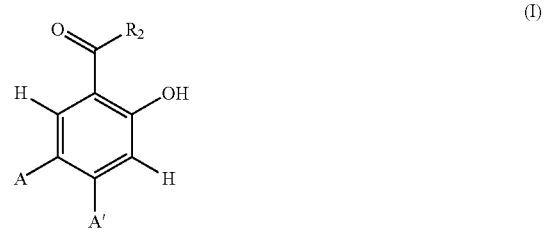

(I)

11 Claims, No Drawings

(56) References Cited

U.S. PATENT DOCUMENTS

2011/0124819 A1   5/2011   Hoelzl

OTHER PUBLICATIONS

Chem. Abst. No. 1991:482101 of JP2251838.
Chem. Abst. No. 2003:401826 of JP2003154762.

* cited by examiner

ANTIMICROBIAL AMINO-SALICYLIC ACID DERIVATIVES

The present invention relates to the use of amino-salicylic acid derivatives in the anti microbial treatment of surfaces, to the use in disinfectants, to corresponding methods and formulations for preservation and/or antimicrobial treatment, especially preservation of cosmetics, household products, textiles and plastics, and to some novel amino-salicylic acid derivatives.

Some compounds of the salicylic acid series containing free primary amino groups, as well as corresponding salicylic esters and salts thereof, have long been known as antibacterial agents. It has now been found that certain N-acylated amino-salicylic acid derivatives possess especially valuable antimicrobial properties and are useful broadband antimicrobials including broad antifungal and antibacterial action.

Present invention thus primarily pertains to a method for achieving an antimicrobial, preservative and/or microorganism adhesion inhibiting effect, for the protection within an article and/or material or on the surface of an article and/or material, which method comprises applying a compound of the formula I

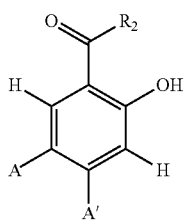
(I)

wherein
one of A and A' is a residue of the formula I'

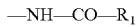 —NH—CO—R$_1$ (I')

while the other is hydrogen;
R$_1$ is C$_1$-C$_{22}$alkyl, C$_3$-C$_{12}$cycloalkyl, C$_3$-C$_{12}$cycloalkyl interrupted by O and/or NR$_5$, C$_4$-C$_{12}$aryl, C$_5$-C$_{18}$arylalkyl;
R$_2$ is OR$_3$ or NHR$_4$;
R$_3$ and R$_4$ are selected from H, C$_1$-C$_{22}$alkyl, C$_3$-C$_{12}$cycloalkyl, C$_3$-C$_{12}$cycloalkyl interrupted by O and/or NR$_5$, C$_4$-C$_{12}$aryl, C$_5$-C$_{18}$arylalkyl;
R$_5$ is H or C$_1$-C$_8$alkyl;
wherein each aryl moiety is unsubstituted or substituted by C$_1$-C$_4$alkyl, C$_1$-C$_4$alkoxy, C$_1$-C$_4$acyl, C$_1$-C$_4$acyloxy, C$_1$-C$_4$acylamino, CF$_3$, OH, amino, halogen;
or an adduct or salt thereof; to said article and/or material.

Consequently, the invention includes compounds of the above formula I as well as their adducts and salts for use as an antimicrobial, especially a bactericide or fungicide.

Present invention further includes the use of a compound of the formula I or its adduct or salt for antimicrobial treatment, antimicrobial accoutrement, preservation, desodoration and/or disinfection of inanimate surfaces and materials; also included is its use as a biocide in technical processes comprising water and/or humidity. These uses of compounds of the formula I according to present invention are generally in fields apart from direct therapeutical methods (i.e. non-therapeutical use). Examples are uses for preventing formation of a microbial biofilm and/or for disaggregation of a microbial biofilm and/or for inhibition of microbial growth and/or for killing of microorganisms capable of building a biofilm., e.g. on technical surfaces or device surfaces, or use as preservative in a technical, cosmetical or pharmaceutical materials or compositions, in order to protect said surfaces, materials and/or compositions from harmful effects of the microorganisms.

Materials or surfaces preserved with the present compounds thus are another embodiment of the present invention, while a further embodiment pertains to formulations or compositions which are useful for the antimicrobial treatment of surfaces (usually by applying the formulations themselves or dilutions thereof, as common to cleansing processes or disinfecting processes or coating processes) or for the antimicrobial accoutrement of materials (as in the case of an antimicrobial additive, which is applied to, or incorporated into the material). The materials, products, formulations or compositions equipped usually contain the present compound(s) in an amount from the range 0.01 to 15% by weight, relative to the overall weight of the material, product, formulation or composition. Examples are:

Cosmetical products or formulations containing (a) a compound of the formula I or its adduct or salt and (b) a cosmetically acceptable carrier;

pharmaceutical products or formulations containing (a) a compound of the formula I or its adduct or salt and (b) a pharmaceutically acceptable carrier;

coating compositions containing (a) a compound of the formula I or its adduct or salt and (b) a film forming binder;

cleansing products or formulations containing (a) a compound of the formula I or its adduct or salt and (b) a surfactant.

Compounds of the formula I, which are preferred for use within the embodiments of the present invention, generally conform to the formula II or III:

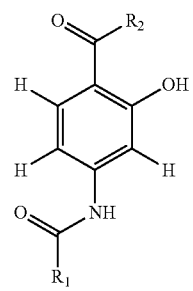
(II)

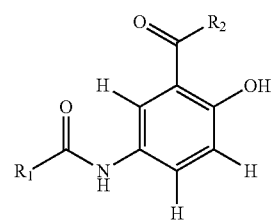
(III)

where R$_1$, R$_2$ generally are as explained for formula I. More preferably in the compounds of the invention, R$_1$ is C$_1$-C$_{12}$alkyl, C$_3$-C$_{12}$cycloalkyl, pyridyl, phenyl, C$_7$-C$_{18}$phenylalkyl. Also more preferred are compounds wherein R$_2$ is OR$_3$ or NHR$_4$. R$_3$ and R$_4$ are preferably selected from H, C$_1$-C$_{12}$alkyl, C$_3$-C$_{12}$cycloalkyl, pyridyl, phenyl, C$_7$-C$_{18}$phenylalkyl.

Compounds of formula III among them are especially preferred.

Adducts useful are generally those with suitable acids or especially bases, which components may be organic or especially inorganic such as HCl, or carbonates, hydrogen carbonates, acetates, sulfates of alkaline or alkaline earth metals or zinc. Salts may include common salts of salicylic acid such as alkaline or alkaline earth salts; or salts of specific functional ions such as silver or zinc salts.

$C_1$-$C_{22}$alkyl generally includes branched and unbranched residues such as methyl, ethyl, propyl, isopropyl, butyl, isobutyl, tert-butyl, pentyl, hexyl, heptyl, octyl, nonyl, decyl, undecyl, dodecyl, tridecyl, tetradecyl, pentadecyl, hexadecyl, heptadecyl, octadecyl, eicosyl, docosyl; preferred are $C_1$-$C_{12}$alkyl, more preferred are unbranched residues (i.e. n-alkyls) such as methyl, ethyl, propyl, butyl, hexyl, heptyl, octyl, nonyl, decyl, undecyl, dodecyl, and especially pentyl.

$C_3$-$C_{12}$cycloalkyl generally includes cyclopentyl, cyclohexyl, cycloheptyl, cyclooctyl, cyclononyl, cyclodecyl, cycloundecyl, cyclododecyl. $C_3$-$C_{12}$cycloalkyl interrupted by O and/or $NR_5$ includes, for example, piperidyl, piperazinyl, morpholinyl.

$C_4$-$C_{12}$aryl generally includes carbocyclic as well as heterocyclic aromatic residues, with N-, O- and N,O-heterocycles being preferred. Any aryl moiety within the present compounds of the formula I or II or III is more preferably selected from phenyl, naphthyl, pyridyl, chinolinyl (especially as

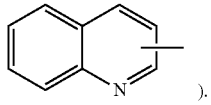

).

$C_5$-$C_{18}$arylalkyl generally includes alkyl substituted by aryl as defined above, with the total number of carbon atoms in the alkyl core and aryl substituent from the range 5-18; preferred is $C_7$-$C_{11}$phenylalkyl such as benzyl. The aryl moiety is preferably unsubstituted or substituted by additional carbon substituents such as alkyl; preferred is phenyl mono-, di- or trisubstituted by $C_1$-$C_4$alkyl.

Some compounds especially useful within the present invention are novel compounds. The invention therefore further includes a compound of the formula III

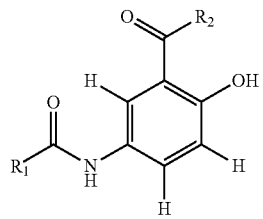

(III)

wherein $R_2$ is OH and $R_1$ is unbranched $C_1$-$C_3$alkyl, unbranched $C_5$-$C_{12}$alkyl, or $C_3$-$C_{12}$cycloalkyl, especially n-pentyl or cyclohexyl, or an adduct or salt thereof.

Materials equipped within the present methods, uses and compositions with aminosalicylic compounds of the invention include, for example, household products such as washing and cleaning formulations, cosmetics, pharmaceutical products, medical device materials, fabrics, plastics, paper, nonwovens, wood, leather. Inanimate surfaces equipped within the present methods, uses and compositions with aminosalicylic compounds of the invention include, for example, medical device surfaces, surfaces of plastic articles, coated surfaces, paper, nonwovens, wood, leather, metal surfaces, surfaces technical products such as electrical devices or water processing equipment.

In many cases, the present compounds of the formula I will be used concomitantly with further agents, and especially the cosmetical or pharmaceutical products, materials, formulations or compositions containing them will consequently contain such further cosmetical or pharmaceutical active ingredients; these are especially selected from:
i) polysaccharides, for example glucanes;
ii) further bactericides and/or preservatives, for example selected from benzoic acid, its salts and esters; propionic acid and its salts; salicylic acid and its salts; sorbic acid and its salts; formaldehyde; paraformaldehyde; o-phenylphenol and its salts; inorganic sulphites and hydrogen sulphites; sodium iodate; chlorobutanol; 4-hydroxybenzoic acid and its salts and esters; 3-acetyl-6-methylpyran-2,4(3H)-dione; formic acid; sodium formiate; dibromohexamidine and its salts; undec-10-enoic acid and salts; hexetidine; 5-bromo-5-nitro-1,3-dioxane; bronopol; 2,4-dichlorobenzyl alcohol; triclocarban; 2.4.4'-trichloro-2'-hydroxy-diphenylether (Triclosan); 4-chloro-3,5-xylenol; imidazolidinyl urea; poly(1-hexamethylenebiguanide hydrochloride); 2-phenoxyethanol; hexamethylenetetramine; methenamine 3-chloroallylochloride; 1-(4-chlorophenoxy)-1-(imidazol-1-yl)-3,3-dimethylbutan-2-one; 1,3-bis(hydroxymethyl)-5,5-dimethylimidazolidine-2,4-dione; benzyl alcohol; 1-hydroxy-4-methyl-6(2,4,4-trimethylpentyl)-2-pyridon or its monoethanolamine salt; methyldibromoglutaronitrile; bromochlorophen; 4-isopropyl-m-cresol; mixture of 5-Chloro-2-methylisothiazol-3(2H)-one and 2-methylisothiazol-3(2H)-one with magnesium chloride and magnesium nitrate; clorophene; 2-chloroacetamide; chlorhexidine and its digluconate, diacetate and/or dihydrochloride; 1-phenoxypropan-2-ol; alkyl ($C_{12}$-$C_{22}$) trimethyl ammonium bromide and/or chloride; 4,4-dimethyl-1,3-oxizalidine; N-(hydroxymethyl)-N-(dihydroxymethyl-1,3-dioxo-2,5-imidazolidinyl-4)-N'-(hydroxymethyl)urea; hexamidine and its salts; glutaraldehyde; chlorphenesin; sodium hydroxymethylglycinate; benzethonium chloride; benzalkonium chloride, bromide and/or saccharinate; benzylhemiformal, listerine, alexidine, and essential oils including thymol, geraniol, carvacrol, citral, hinokitiol, eucalyptol, eugenol, menthol, catechol, lactic acid, lactates, 1,2-pentanediol;
iii) antiphlogistic agents, antiinflammatory agents, antipsoriatic agents, further skin actives, cell proliferation regulators, antiallergic agents, DNA-protectants;
iv) vitamins, antioxidants, UV protecting agents, moisturizing agents, antiaging agents, emollients, thickening agents, moisture-retention agents, film formers, perfumes and colourants.

Depending upon the form of the personal care preparation, it comprises, in addition to the antimicrobial compounds of the invention, further constituents, for example sequestering agents, colourings, perfume oils, thickening or solidifying agents (consistency regulators), emulsifiers, emollients, UV-absorbers, skin protective agents, antioxidants, additives that improve the mechanical properties, such as dicarboxylic acids and/or aluminium, zinc, calcium or magnesium salts of $C_{14}$-$C_{22}$ fatty acids, and, optionally, preservatives.

The product or formulation according to the invention thus preferably is:
an antibacterial composition for contact with the mucosa or other tissues of the oral cavity,
a shampoo,
a hair conditioner,
a fabric care formulation,
a surface disinfectant,
a cosmetical or dermatological skin composition,
a feminine hygiene composition such as a feminine hygiene washing lotion or spray,
a composition for the treatment of a medical and especially oral implant, denture, brace,
an eye drop formulation,
an eye make-up or an eye make-up remover,
a tooth paste or gel,
a mouth wash,
a gargle,
an inhalant,
an adhesive paste,
an anti-inflammatory skin care preparation,
a sunscreen lotion,
an after-sun skin care preparation,
a revitalizing skin care preparation,
an anti-aging skin care preparation,
a wound healing formulation,
especially in the form of an aqueous paste or gel or a liquid such as an aqueous liquid or viscous liquid.

For the treatment or disinfection of surfaces, the compound of formula I is usually applied in an amount ranging from 0.1 to 100000 mg per square meter surface. For the sake of clarity it is noted that the present methods and uses generally are non-therapeutical ones.

Application of the present compounds and/or formulations usually follows known methods; for example, surfaces may be treated e.g. by spraying, dipping; bulk materials are commonly equipped with the present compounds in powder form or in form of solutions or dispersions e.g. by commonly known mixing or kneading processes.

Present compounds are preferably for use in the antimicrobial treatment, antimicrobial accoutrement, desodoration and/or disinfection of skin, mucosa, tooth surfaces, nails, hair; especially as an antimicrobial active against infection of the skin, mucosal membranes, nails, or as an active for treatment of injuries of the skin and/or mucosal membranes.

The compounds of the invention also exhibit pronounced antimicrobial action, for example, against pathogenic gram-positive and gram-negative bacteria and against bacteria of the skin and oral flora, and also against yeasts and molds. They are accordingly suitable for disinfection, deodorisation, and for general and antimicrobial treatment of the skin and mucosa and of integumentary appendages (hair), for example, for the disinfection of hands and wounds.

They are accordingly suitable as antimicrobial active substances and preservatives in personal care preparations, for example shampoos, bath additives, hair care preparations, liquid and solid soaps (based on synthetic surfactants and salts of saturated and/or unsaturated fatty acids), lotions and creams, deodorants, other aqueous or alcoholic solutions, e.g. cleansing solutions for the skin, moist cleaning cloths, wet wipes, oils or powders.

For example, the antimicrobial compounds of the invention are effective as anti-dandruff agents in shampoos or other products used in hair treatment such as oils, sprays, hair gels. Moreover they can be used as agent against dermatophytes for use in products against seborrheic dermatitis, psoriasis and athletes foot in formulation types such as creams, lotions, gels, powders, oils, tonics, sprays, wet wipes etc. And as anti-acne agents in facial care products such as creams, lotions, gels, tonics, powders etc.

The invention accordingly relates also to a personal care preparation comprising at least one antimicrobial compound of the invention and cosmetically tolerable carriers or adjuvants.

The personal care preparation according to the invention contains from 0.01 to 15% by weight, for example, from 0.1 to 10% by weight, based on the total weight of the inventive composition, of the antimicrobial compounds of the invention, and cosmetically tolerable adjuvants.

The personal care preparation according to the invention may be in the form of a water-in-oil or oil-in-water emulsion, an alcoholic or alcohol-containing formulation, a vesicular dispersion of an ionic or non-ionic ampiphilic lipid, a gel, a solid stick or an aerosol formulation.

As a water-in-oil or oil-in-water emulsion, the cosmetically tolerable adjuvant contains preferably from 5 to 50% of an oil phase, from 5 to 20% of an emulsifier and from 30 to 90% water. The oil phase may comprise any oil suitable for cosmetic formulations, for example one or more hydrocarbon oils, a wax, a natural oil, a silicone oil, a fatty acid ester or a fatty alcohol. Preferred mono- or poly-ols are ethanol, isopropanol, propylene glycol, hexylene glycol, glycerol and sorbitol.

Cosmetic formulations according to the invention are used in various fields. There come into consideration, for example, the following preparations:
skin-care preparations, e.g. skin-washing and cleansing preparations in the form of tablet-form or liquid soaps, synthetic detergents or washing pastes,
bath preparations, e.g. liquid (foam baths, milks, shower preparations) or solid bath preparations, e.g. bath cubes and bath salts;
skin-care preparations, e.g. skin emulsions, multi-emulsions or skin oils;
cosmetic personal care preparations, e.g. facial make-up in the form of day creams or powder creams, face powder (loose or pressed), rouge or cream make-up, eye-care preparations, e.g. eye shadow preparations, mascaras, eyeliners, eye creams or eye-fix creams; lip-care preparations, e.g. lipsticks, lip gloss, lip contour pencils, nail-care preparations, such as nail varnish, nail varnish removers, nail hardeners or cuticle removers;
intimate hygiene preparations, e.g. intimate washing lotions or intimate sprays;
foot-care preparations, e.g. foot baths, foot powders, foot creams or foot balsams, special deodorants and antiperspirants or callus-removing preparations;
light-protective preparations, such as sun milks, lotions, creams or oils, sun-blocks or tropicals, pre-tanning preparations or after-sun preparations;
skin-tanning preparations, e.g. self-tanning creams;
depigmenting preparations, e.g. preparations for bleaching the skin or skin-lightening preparations;
insect-repellents, e.g. insect-repellent oils, lotions, sprays or sticks;
deodorants, such as deodorant sprays, pump-action sprays, deodorant gels, sticks or roll-ons;
antiperspirants, e.g. antiperspirant sticks, creams or roll-ons;

preparations for cleansing and caring for blemished skin, e.g. synthetic detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams and gels, preshave preparations for dry shaving, aftershaves or aftershave lotions;

fragrance preparations, e.g. fragrances (eau de Cologne, eau de toilette, eau de parfum, parfum de toilette, perfume), perfume oils or perfume creams;

dental care, denture-care and mouth-care preparations, e.g. toothpastes, gel toothpastes, tooth powders, mouthwash concentrates, anti-plaque mouthwashes, denture cleaners or denture fixatives;

cosmetic hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colorants, preparations containing self-oxidising dyes, or natural hair colorants, such as henna or camomile.

The invention relates also to oral compositions containing from 0.01 to 15% by weight, based on the total weight of the composition, of the antimicrobial compound, and orally tolerable adjuvants.

The oral composition according to the invention may be, for example, in the form of a gel, a paste, a cream or an aqueous preparation (mouthwash).

The oral composition according to the invention may also comprise compounds that release fluoride ions which are effective against the formation of caries, for example inorganic fluoride salts, e.g. sodium, potassium, ammonium or calcium fluoride, or organic fluoride salts, e.g. amine fluorides, which are known under the trade name OLAFLUOR.

The anti-microbial compounds of this invention are also suitable for treating, especially preserving, textile fibre materials. Such materials are undyed and dyed or printed fibre materials, e.g. of silk, wool, polyamide or polyurethanes, and especially cellulosic fibre materials of all kinds. Such fibre materials are, for example, natural cellulose fibres, such as cotton, linen, jute and hemp, as well as cellulose and regenerated cellulose.

The antimicrobial compounds of this invention are suitable also for treating, especially imparting antimicrobial properties to or preserving, plastics, e.g. polyethylene, polypropylene, polyurethane, polyester, polyamide, polycarbonate, latex etc. Fields of use therefore are, for example, floor coverings, plastics coatings, plastics containers and packaging materials; kitchen and bathroom utensils (e.g. brushes, shower curtains, sponges, bathmats), latex, filter materials (air and water filters), plastics articles used in the field of medicine, e.g. dressing materials, syringes, catheters etc., so-called "medical devices", gloves and mattresses.

The antimicrobial compounds of this invention are suitable also for treating, especially imparting antimicrobial properties to or preserving industrial formulations such as coatings, lubricants etc.

Paper, for example papers used for hygiene purposes, may also be provided with antimicrobial properties using the present anti-microbial compounds.

It is also possible for nonwovens, e.g. nappies/diapers, sanitary towels, panty liners, and cloths for hygiene and household uses, to be provided with antimicrobial properties in accordance with the invention.

The antimicrobial compounds of this invention are also used in washing and cleaning formulations, e.g. in liquid or powder washing agents or softeners.

The antimicrobial compounds of this invention can also be used in household and general-purpose cleaners for cleaning and disinfecting hard surfaces.

In addition to preserving cosmetic and household products, the preservation of technical products, the provision of technical products with antimicrobial properties and use as a biocide in technical processes are also possible, for example in paper treatment, especially in paper treatment liquors, printing thickeners of starch or cellulose derivatives, surface-coatings and paints.

The antimicrobial compounds of the invention are also suitable for the antimicrobial treatment of wood and for the antimicrobial treatment of leather, the preserving of leather and the provision of leather with antimicrobial properties.

The compounds according to the invention are also suitable for the protection of cosmetic products, pharmaceutical products and household products from microbial damage.

The compounds claimed in the present invention can be combined with biocides used as antimicrobial actives in cosmetic and pharmaceutical products and household products and/or preservatives used in cosmetic and pharmaceutical products or household products in order to improve the antimicrobial activity of the cosmetic product, the pharmaceutical product or household product.

In addition, the compounds are capable of penetrating biofilms on living and non-living surfaces, of preventing the adhesion of bacteria to surfaces and any further build-up of the biofilm, of detaching such biofilm and/or inhibiting the further growth of the biofilm-forming micro-organisms in the biological matrix, or of killing such micro-organisms.

Biofilms are understood, very generally, to be aggregations of living and dead micro-organisms, especially bacteria, that adhere to living and non-living surfaces, together with their metabolites in the form of extracellular polymeric substances (EPS matrix), e.g. polysaccharides. The activity of antimicrobial substances that normally exhibit a pronounced growth-inhibiting or lethal action with respect to planktonic cells may be greatly reduced with respect to microorganisms that are organized in biofilms, for example because of inadequate penetration of the active substance into the biological matrix.

In the present invention, this may relate to biofilms on human tooth surfaces and oral mucosa, which play a crucial role in the onset of degenerative diseases in the oral cavity, e.g. caries or periodontitis, as a result of the biofilm-forming micro-organisms or their metabolites.

Action against bio-films in the present invention also relates to biofilms on non-human surfaces. The antimicrobial compounds of this invention are useful in coatings or films in protecting surfaces from bio-fouling. Such surfaces include surfaces in contact with marine environments (including fresh water, brackish water and salt water environments), for example, the hulls of ships, surfaces of docks or the inside of pipes in circulating or pass-through water systems. Other surfaces are susceptible to similar biofouling, for example walls exposed to rain water, walls of showers, roofs, gutters, pool areas, saunas, floors and walls exposed to damp environs such as basements or garages and even the housing of tools and outdoor furniture.

The antimicrobial compounds of this invention are also useful in preventing bio-fouling, or eliminating or controlling microbe accumulation on the surfaces either by incorporating the antimicrobial compounds into the article or surface of the article in question or by applying the antimicrobial to these surfaces as part of a coating or film.

When applied as a part of a film or coating, the antimicrobial compounds of this invention are part of a composition which also comprises a binder.

The binder may be any polymer or oligomer compatible with the present antimicrobials. The binder may be in the form of a polymer or oligomer prior to preparation of the anti-fouling composition, or may form by polymerization during or after preparation, including after application to the substrate. In certain applications, such as certain coating applications, it will be desirable to crosslink the oligomer or polymer of the anti fouling composition after application.

The term binder as used in the present invention also includes materials such as glycols, oils, waxes and surfactants commercially used in the care of wood, plastic, glass and other surfaces. Examples include water proofing materials for wood, vinyl protectants, protective waxes and the like.

The composition may be a coating or a film. When the composition is a thermoplastic film which is applied to a surface, for example, by the use of an adhesive or by melt applications including calendaring and co-extrusion, the binder is the thermoplastic polymer matrix used to prepare the film.

When the composition is a coating, it may be applied as a liquid solution or suspension, a paste, gel, oil or the coating composition may be a solid, for example a powder coating which is subsequently cured by heat, UV light or other method.

As the composition of the invention may be a coating or a film, the binder can be comprised of any polymer used in coating formulations or film preparation. For example, the binder is a thermoset, thermoplastic, elastomeric, inherently crosslinked or crosslinked polymer.

Thermoset, thermoplastic, elastomeric, inherently crosslinked or crosslinked polymers include polyolefin, polyamide, polyurethane, polyacrylate, polyacrylamide, polycarbonate, polystyrene, polyvinyl acetates, polyvinyl alcohols, polyester, halogenated vinyl polymers such as PVC, natural and synthetic rubbers, alkyd resins, epoxy resins, unsaturated polyesters, unsaturated polyamides, polyimides, silicon containing and carbamate polymers, fluorinated polymers, crosslinkable acrylic resins derived from substituted acrylic esters, e.g. from epoxy acrylates, urethane acrylates or polyester acrylates. The polymers may also be blends and copolymers of the preceding chemistries.

Biocompatible coating polymers, such as, poly[alkoxyalkanoate-co-3-hydroxyalkenoate] (PHAE) polyesters, Geiger et. al. Polymer Bulletin 52, 65-70 (2004), can also serve as binders in the present invention.

Alkyd resins, polyesters, polyurethanes, epoxy resins, silicone containing polymers, polyacrylates, polyacrylamides, fluorinated polymers and polymers of vinyl acetate, vinyl alcohol and vinyl amine are non-limiting examples of common coating binders useful in the present invention. Other coating binders, of course, are part of the present invention.

Coatings are frequently crosslinked with, for example, melamine resins, urea resins, isocyanates, isocyanurates, polyisocyanates, epoxy resins, anhydrides, poly acids and amines, with or without accelerators.

The compositions of present invention are for example a coating applied to a surface which is exposed to conditions favorable for bioaccumulation. The presence of the antimicrobial compounds of this invention in said coating will prevent the adherence of organisms to the surface.

The anti-microbial compounds of the present invention may be part of a complete coating or paint formulation, such as a marine gel-coat, shellac, varnish, lacquer or paint, or the anti fouling composition may comprise only a polymer of the instant invention and binder, or a polymer of the instant invention, binder and a carrier substance. It is anticipated that other additives encountered in such coating formulations or applications will find optional use in the present applications as well.

The coating may be solvent borne or aqueous. Aqueous coatings are typically considered more environmentally friendly.

The coating is, for example, aqueous dispersion of a polymer of the instant invention and a binder or a water based coating or paint. For example, the coating comprises an aqueous dispersion of a polymer of the instant invention and an acrylic, methacrylic or acrylamide polymers or co-polymers or a poly[alkoxyalkanoate-co-3-hydroxyalkenoate]polyester.

The coating may be applied to a surface which has already been coated, such as a protective coating, a clear coat or a protective wax applied over a previously coated article.

Coating systems include marine coatings, wood coatings, other coatings for metals and coatings over plastics and ceramics. Exemplary of marine coatings are gel coats comprising an unsaturated polyester, a styrene and a catalyst.

The coating is, for example a house paint, or other decorative or protective paint. It may be a paint or other coating that is applied to cement, concrete or other masonry article. The coating may be a water proofer as for a basement or foundation.

The coating composition is applied to a surface by any conventional means including spin coating, dip coating, spray coating, draw down, or by brush, roller or other applicator. A drying or curing period will typically be needed.

Coating or film thickness will vary depending on application and will become apparent to one skilled in the art after limited testing.

The composition may be in the form of a protective laminate film.

Such a film typically comprises thermoset, thermoplastic, elastomeric, or crosslinked polymers. Examples of such polymers include, but are not limited to, polyolefin, polyamide, polyurethane, polyacrylate, polyacrylamide, polycarbonate, polystyrene, polyvinyl acetates, polyvinyl alcohols, polyester, halogenated vinyl polymers such as PVC, natural and synthetic rubbers, alkyl resins, epoxy resins, unsaturated polyesters, unsaturated polyamides, polyimides, fluorinated polymers, silicon containing and carbamate polymers. The polymers may also be blends and copolymers of the preceding chemistries.

When the anti-fouling composition is a preformed film it is applied to the surface by, for example, the use of an adhesive, or co-extruded onto the surface. It may also be mechanically affixed via fasteners which may require the use of a sealant or caulk wherein the esters of the instant invention may also be advantageously employed.

A plastic film may also be applied with heat which includes calendaring, melt applications and shrink wrapping.

The composition may be part of a polish, such a furniture polish, or a dispersant or surfactant formulation such as a glycol or mineral oil dispersion or other formulation as used in for example wood protection.

Examples of useful surfactants include, but are not limited to, polyoxyethylene-based surface-active substances, including polyoxyethylene sorbitan tetraoleate (PST), polyoxyethylene sorbitol hexaoleate (PSH), polyoxyethylene 6 tridecyl ether, polyoxyethylene 12 tridecyl ether, polyoxyethylene 18 tridecyl ether, TWEEN® surfactants, TRITON® surfactants, and the polyoxyethlene-polyoxypropylene copolymers such as the PLURONIC® and POLOXAMER® product series (from BASF). Other matrix-forming components include dextrans, linear PEG molecules (MW 500 to 5,000,000), star-shaped PEG molecules, comb-shaped and dendrimeric, hyperbrached PEG molecules, as well as the analogous linear, star, and dendrimer polyamine polymers, and various carbonated, per-fluorinated (e.g., DUPONT ZONYL® fluorosurfactants) and siliconated (e.g, dimethylsiloxane-ethylene oxide block copolymers) surfactants.

Given the wide array of applications for the present anti-microbial compositions, the composition may contain other additives such as antioxidants, UV absorbers, hindered amines, phosphites or phosphonites, benzofuran-2-ones, thiosynergists, polyamide stabilizers, metal stearates, nucleating agents, fillers, reinforcing agents, lubricants, emulsifiers, dyes, pigments, dispersants, other optical brighteners, flame retardants, antistatic agents, blowing agents and the like, such as the materials listed below, or mixtures thereof.

The substrate can be an inorganic or organic substrate, for example, a metal or metal alloy; a thermoplastic, elastomeric, inherently crosslinked or crosslinked polymer as described above; a natural polymer such as wood or rubber; a ceramic material; glass; leather or other textile.

The substrate may be, for example, non-metal inorganic surfaces such as silica, silicon dioxide, titanium oxides, aluminum oxides, iron oxides, carbon, silicon, various silicates and sol-gels, masonry, and composite materials such as fiberglass and plastic lumber (a blend of polymers and wood shavings, wood flour or other wood particles).

The inorganic or organic substrate is, for example, a metal or metal alloy, a thermoplastic, elastomeric, inherently crosslinked or crosslinked polymer, a ceramic material or a glass.

The substrate may be a multi-layered article comprised of the same or different components in each layer. The surface coated or laminated may be the exposed surface of an already applied coating or laminate.

The inorganic or organic substrate to be coated or laminated can be in any solid form.

For example, polymer substrates may be plastics in the form of films, injection-molded articles, extruded workpieces, fibres, felts or woven fabrics.

For example molded or extruded polymeric articles used in construction or the manufacture of durable goods such as siding, fascia and mailboxes can all benefit from the present method for stabilizer replenishment.

Plastics which would benefit from the present method include, but are not limited to, plastics used in construction or the manufacture of durable goods or machine parts, including outdoor furniture, boats, siding, roofing, glazing, protective films, decals, sealants, composites like plastic lumber and fiber reinforced composites, functional films including films used in displays as well as articles constructed from synthetic fibers such as awnings, fabrics such as used in canvas or sails and rubber articles such as outdoor matting and other uses cited in this disclosure. Exemplary of such plastics are polypropylene, polyethylene, PVC, POM, polysulfones, styrenics, polyamides, urethanes, polyesters, polycarbonate, acrylics, butadiene, thermoplastic polyolefins, ionomers, unsaturated polyesters and blends of polymer resins including ABS, SAN and PC/ABS.

The anti-microbial compounds of the invention are also effective in protecting useful plants, such as plants in agriculture, in horticulture and in forests, plant parts and seeds from disease and spoilage. For example, the present invention also provides a method which comprises applying to useful plants, the locus thereof or propagation material thereof a composition which comprises at least one of the polyglycerol polymers and co-polymers of the invention. Said compositions can be used as foliar, soil and seed treatment fungicides.

The compositions of the invention it is possible to inhibit or destroy the phytopathogenic microorganisms which occur in plants or in parts of plants (fruit, blossoms, leaves, stems, tubers, roots) in different useful plants. The present compositions are applied by treating the fungi, the useful plants, the locus thereof, the propagation material thereof, the natural substances of plant origin, which have been taken from the natural life cycle, and/or their processed forms, or the industrial materials threatened by fungus attack with the compositions in an effective amount.

The compositions according to the invention may be applied before or after infection of the useful plants, the propagation material thereof, the natural substances of plant and/or animal origin, which have been taken from the natural life cycle, and/or their processed forms, or the industrial materials by the fungi.

The compositions of the present invention are of particular interest for controlling a large number of fungi in various useful plants or their seeds, especially in field crops such as potatoes, tobacco and sugarbeets, and wheat, rye, barley, oats, rice, maize, lawns, cotton, soybeans, oil seed rape, pulse crops, sunflower, coffee, sugarcane, fruit and ornamentals in horticulture and viticulture, in vegetables such as cucumbers, beans and cucurbits.

When applied to plants, the anti-microbial compounds of the invention are applied at a rate of 1 to 5000 g a.i./ha, for example 2 to 2000 g a.i./ha, for example, 5 to 2000 g a.i./ha, for example, 10 to 1000 g a.i./ha, e.g. 50, 75, 100, 200, 250, 500, 800, 1000, 1500 g a.i./ha of polymer or co-polymers.

In agricultural practice the application rates depend on the type of effect desired, and typically range from 20 to 4000 g of total antimicrobials per hectare.

When treating seed, rates of 0.001 to 50 g of the present anti-microbial compounds, for example 0.01 to 10 g, per kg of seed, are generally sufficient.

The composition comprising the anti-microbial compounds of the invention may be employed in any conventional form, for example in the form a powder for dry seed treatment (DS), an emulsion for seed treatment (ES), a flowable concentrate for seed treatment (FS), a solution for seed treatment (LS), a water dispersible powder for seed treatment (WS), a capsule suspension for seed treatment (CF), a gel for seed treatment (GF), an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP) or any technically feasible formulation in combination with agriculturally acceptable adjuvants.

Such compositions may be produced in conventional manner, e.g. by mixing the active ingredients with appropriate formulation inerts (diluents, solvents, fillers and optionally other formulating ingredients such as surfactants, biocides, anti-freeze, stickers, thickeners and compounds that provide adjuvancy effects). For example, formulations to be applied in spraying forms, such as water dispersible concentrates (e.g. EC, SC, DC, OD, SE, EW, EO and the like), wettable powders and granules, typically contain surfactants such as wetting and dispersing agents and other compounds that provide adjuvancy effects.

A seed dressing formulation is applied in a manner known per se to the seeds employing the combination of the invention and a diluent in suitable seed dressing formulation form, e.g. as an aqueous suspension or in a dry powder form having good adherence to the seeds. Such seed dressing formulations are known in the art. Seed dressing formulations may contain the single active ingredients or the combination of active ingredients in encapsulated form, e.g. as slow release capsules or microcapsules.

In general, the formulations include from 0.01 to 90% by weight of at least one of the anti-microbial compounds, from 0 to 20% agriculturally acceptable surfactant and 10 to 99.99% solid or liquid formulation inerts and adjuvant(s), and optionally other active agents, particularly microbiocides or conservatives or the like. Concentrated forms of compositions generally contain in between about 2 and 80%, for example, between about 5 and 70% by weight of total active agent. Application forms of formulation may for example contain from 0.01 to 20% by weight, for example from 0.01 to 5% by weight of active agent.

Methods of preparing the above plant protection formulations are well known, for example, in US Published Pat. Appl. 20070265267, already incorporated by reference.

Particular embodiments of the invention therefore relate to methods for protecting plastics, coatings, other materials of construction, home or personal care formulations, plants, agricultural products, industrial formulations or technical process against the action of microbes which comprises adding an effective amount of the anti-microbial compounds of the present invention;

a method for protecting skin, mucosa and integumentary appendages against the action of microbes including protecting the scalp from dandruff, which comprises applying a preparation comprising an effective amount of the anti-microbial compounds of the present invention;

a method for protecting paper, wood, leather, synthetic textile materials or natural textile materials such as cotton against the action of microbes comprising incorporating or applying an effective amount of the present polymer or copolymer or a composition comprising an effective amount the anti-microbial compounds of the present invention;

a method for cleaning and disinfecting hard surfaces which comprises applying a preparation comprising an effective amount of the anti-microbial compounds of the present invention;

a method for preventing bio-fouling of an article comprising incorporating anti-microbial compounds of the present invention into the article or surface of the article or by applying the anti-microbial compounds of the present invention to these surfaces either directly or as part of a coating or film.

Other materials of construction include, in addition to wood, metals, paper, glass, ceramics, coatings, plastics and textiles, materials such as concrete, cement, adhesives, caulking materials, composites of natural and synthetic materials etc.

The amino-salicylic acid derivatives according to the invention are prepared according to processes known per se, generally by acylating amino-salicylic acid in a suitable solvent, preferably a polar solvent such as water, acetone, acetonitrile, dioxane, chloroform, tetrahydrofurane, dimethylformamide, diethylether, or a mixture of such solvents, with the appropriate acyl halide in the presence of an organic or inorganic base, preferably alkaline (e.g. potassium) carbonate:

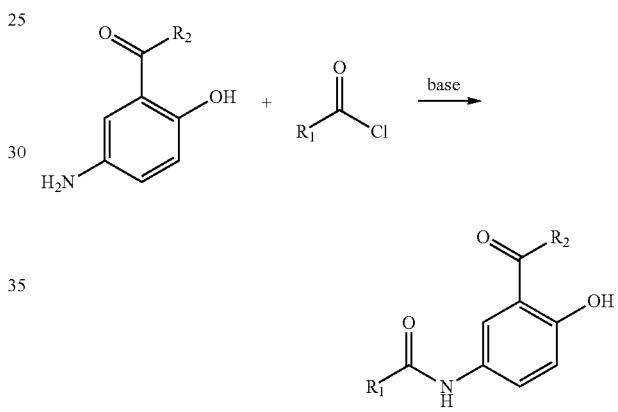

The following examples illustrate the invention. Unless indicated otherwise, percentages refer to percent by weight (b.w.), room temperature denotes a temperature from the range 20-24° C. The determination of bactericidal activity and fungicidal activity in surfactants or shampoo formulations of the present invention is measured in a suspension test according to trivial modifications of the European Standard methods EN 1040 and EN 1275, respectively.

EXAMPLE 1

Preparation of 5-hexanoylamino-salicylic acid (compound 596)

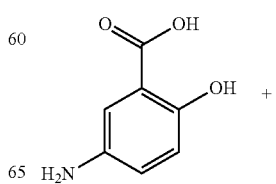

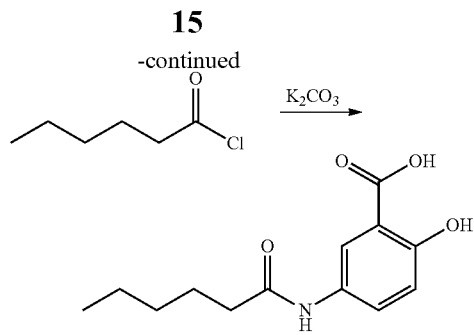

9.18 g (60.0 mmol) 5-amino-salicylic acid and 12.45 g (90.0 mmol) potassium carbonate are suspended in a mixture of 60 ml acetone and 120 ml water. After gas evolution has ceased, the solution is cooled to 0° C. and 10.11 g (75.0 mmol) hexanoic acid chloride is slowly added under vigorous stirring. After stirring at 0° C. for 2 h the mixture is warmed to room temperature and poured onto 300 ml ice/water. The product is filtered, washed with water and dried in vacuum. Purification is achieved by recrystallisation from ethanol, yielding 8.95 g of the above product as a white powder.

1H-NMR (DMSO-d6, [ppm]): 16.1 (s, 1H, OH), 9.40 (s, 1H, NH), 7.75 (s, 1H, =CH), 7.45 (m, 1H, =CH), 6.45 (d, 1H, =CH), 2.20 (t, 2H, CH2), 1.55 (m, 2H, CH2), 1.30 (m, 4H, CH2), 0.85 (t, 3H, CH3)

EXAMPLE 2

Preparation of 5-cyclohexanoylamino-salicylic acid (compound 601)

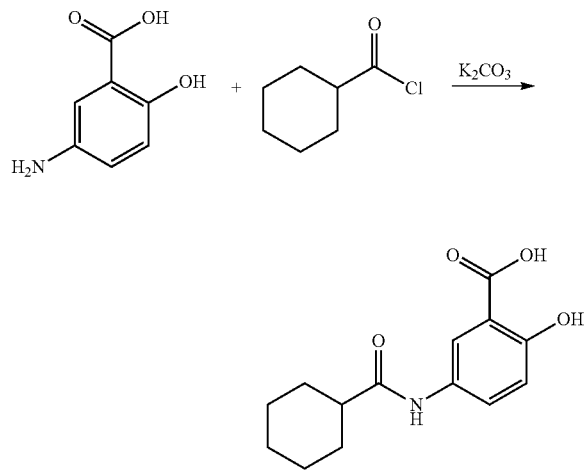

The compound is prepared analogously to example 1 by reacting 56.8 g (360 mmol) 5-amino-salicylic acid, 75.4 g (540 mmol) K2CO3 and 68.0 (450 mmol) cyclohexanecarboxylic acid chloride in 360 ml water/720 ml acetone, yield 60.0 g.

1H-NMR (DMSO-d6, [ppm]): 9.80 (s, 1H, NH), 7.75 (s, 1H, =CH), 7.45 (m, 1H, =CH), 6.45 (d, 1H, =CH), 2.30 (m, 1H, CH), 1.05-1.80 (m, 10H, CH2)

EXAMPLE 3

Further Compounds are Prepared in Analogy to the Methods Described in Examples 1 and 2

TABLE 1

Compounds of the invention (examples)

| structure | compound No. |
|---|---|
| 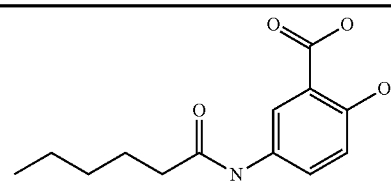 | 596 |
| 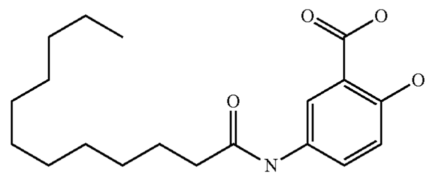 [SMILES: CCCCCCCCCCCC(=O)Nc1ccc(O)c(C(=O)O)c1] | 597 |
| 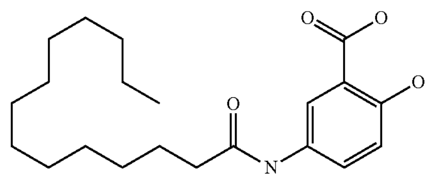 [SMILES: CCCCCCCCCCCCCC(=O)Nc1ccc(O)c(C(=O)O)c1] | 598 |
| 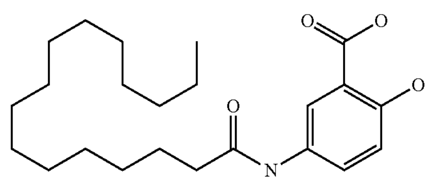 [SMILES: CCCCCCCCCCCCCCCC(=O)Nc1ccc(O)c(C(=O)O)c1] | 599 |
| 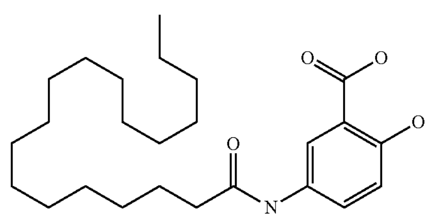 [SMILES: CCCCCCCCCCCCCCCCCC(=O)Nc1ccc(O)c(C(=O)O)c1] | 600 |
| 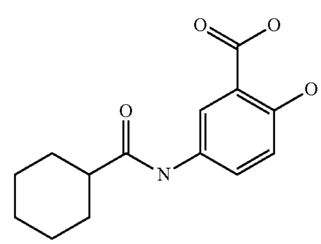 [SMILES: O=C(O)c1cc(NC(=O)C2CCCCC2)ccc1O] | 601 |
| 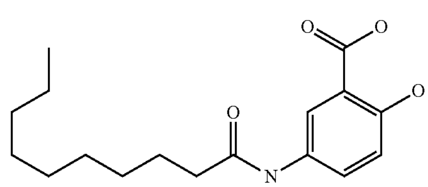 [SMILES: CCCCCCCCCC(=O)Nc1ccc(O)c(C(=O)O)c1] | 602 |

EXAMPLE 4

Bactericidal Efficacy

The bactericidal activity of the compounds of the present invention is measured in a suspension test (trivial modification of the European Standard method EN 1040). Substances listed in Table 1 are tested against gram positive and gram negative bacteria. Results are shown below.

The compound of the invention is dissolved in ethanol resulting in a 1% b.w. stock solution. The cell densities of the bacterial suspensions used as inoculums for the suspension test are as follows (cfu=colony forming units):

| | |
|---|---|
| Staphylococcus aureus ATCC 6538 | $2.0 \times 10^8$ cfu/ml |
| Escherichia coli ATCC 10536 | $3.4 \times 10^8$ cfu/ml |
| Pseudomonas aeruginosa ATCC15442 | $1.9 \times 10^8$ cfu/ml |

For the suspension tests, an appropriate concentration of the test compound is mixed with a bacterial suspension resulting in a final cell count in the mixture of about $10^7$ cfu/ml. These test mixtures are incubated at room temperature (22° C.+/−2° C.) and aliquots of 1 ml test mixture containing the test bacteria are taken after set contact times for determination of the residual cell count of test bacteria. For inactivation of the antimicrobial compounds, the 1 ml aliquots are diluted in 1:10 steps with an aqueous solution containing 10% of Tween 80 (a polyethoxylated sorbitan ester surfactant), 3% lecithin, 0.1% histidine and 0.5% sodium thiosulfate.

The results of the determination of residual cell counts are given in the below table A.

TABLE A

Results of the suspension tests conducted to determine microbicidal activities:

| Test Compound (concentration tested) | Test Organism (cfu/ml and log reduction after set contact times) Contact Time | | | |
|---|---|---|---|---|
| | S. aureus 30 min | E. coli 30 min | P. aeruginosa 30 min | C. albicans 24 h |
| 596 | <100 >5 | <100 >5 | <100 >5 | <100 >4 |
| | S. aureus 24 h | | | |
| 597 | $1.6 \times 10^3$ >5 | | | |
| | S. aureus 24 h | E. coli 24 h | P. aeruginosa 24 h | |
| 601 | <100 >5 | $9.1 \times 10^2$ 4.3 | $6.1 \times 10^2$ 4.8 | |

The results show a strong microbicidal activity of the tested amino-salicylic acid derivatives.

EXAMPLE 5

Fungicidal Activity

The fungicidal activity of the compounds of the present invention is measured in a suspension test (trivial modification of the European Standard method EN 1275).

The compound of the invention is dissolved in ethanol resulting in a 1% b.w. solution of the compound.

The cell density of Candida albicans ATCC 10231 used as inoculum for the suspension test is $2.1 \times 10^7$ cfu/ml.

The compound of the invention is incorporated in an anionic surfactant, for example sodium laureth sulphate (Epicol ESB 70), or a non-ionic surfactant such as decyl glucoside (Plantacare 2000UP), or an amphoteric surfactant, for example cocamidopropyl betaine (Tego Betain F50).

Each of the surfactants is tested at 10% a.i.

Furthermore, the 5-amino-salicylic acid derivatives of the invention are incorporated in a typical shampoo formulation with the following composition:

0.01 to 5% by weight of 5 amino-salicylic acid derivative, 7.0% by weight sodium laureth-2-sulfate, 2.5% by weight decyl glucoside 4.0% by weight cocamidopropyl betaine, 1.0% by weight NaCl and water ad 100%.

pH 6 is adjusted with NaOH.

The surfactant solutions and shampoo formulations tested contain 1% b.w. of the compound of the invention.

The cell densities of the bacterial suspensions used as inoculums for the suspension tests are as follows (cfu=colony forming units):

| | |
|---|---|
| Staphylococcus aureus ATCC 6538 | $2.0 \times 10^8$ cfu/ml |
| Escherichia coli ATCC 10536 | $3.4 \times 10^8$ cfu/ml |
| Pseudomonas aeruginosa ATCC 15442 | $1.9 \times 10^8$ cfu/ml |
| Candida albicans AJCC 10231 | $2.6 \times 10^8$ cfu/ml |
| Aspergillus niger ATCC 6275 | $1.6 \times 10^7$ cfu/ml |

The cell density in the test is adjusted to $10^5$ cfu/ml. These test mixtures are incubated at room temperature (22° C.+/− 2° C.) and aliquots of 1 ml test mixture are taken after set contact times for determination of the residual cell count.

For inactivation of the antimicrobial compounds, the 1 ml aliquots are diluted in 1:10 steps with an aqueous solution containing 10% Tween 80 (a polyethoxylated sorbitan ester surfactant), 3% lecithin, 0.1% histidine and 0.5% sodium thiosulfate.

The results of the determination of residual cell counts are given in the below table B.

TABLE B

Results of the suspension tests conducted to determine the microbicidal activities of compound 596 in surfactants and shampoo

| Test Compound (concentration tested) ID596 | Test Organism (cfu/ml and log reduction after set contact times are given in the table Contact Time | | | | |
|---|---|---|---|---|---|
| | S. aureus 24 h | E. coli 24 h | P. aeruginosa 24 h | C. albicans 24 h | A. niger 7 days |
| anionic surfactant (sodium laureth sulfate) | <100 >3 | <100 >3 | <100 >3 | $1.4 \times 10^4$ 1.2 | $1.7 \times 10^3$ 2.1 |
| non-ionic surfactant (decyl glucoside) | <100 >3 | <100 >3 | <100 >3 | <100 >3 | $1.9 \times 10^4$ 1.1 |
| amphoteric surfactant (cocamidopropyl betaine) | <100 >3 | <100 >3 | <100 >3 | <100 >3 | $1.2 \times 10^3$ 2.3 |
| Shampoo fomulation | <100 >3 | <100 >3 | | | |

The suspension tests show a strong microbicidal activity of the tested compounds against bacteriae and fungi.

The invention claimed is:

1. A method for achieving an antimicrobial, preservative and/or microorganism adhesion inhibiting effect for protection within an article and/or material or on the surface of an article and/or material, which method comprises:
applying a compound of formula I or an adduct or salt thereof to the article and/or the material in an amount effective to protect against action of microbes, wherein

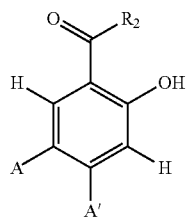

(I)

one of A and A' is a residue of the formula I'

—NH—CO—$R_1$   (I')

while the other is hydrogen;
$R_1$ is $C_1$-$C_{22}$alkyl, $C_3$-$C_{12}$cycloalkyl, $C_3$-$C_{12}$cycloalkyl interrupted by O and/or $NR_5$, $C_4$-$C_{12}$aryl, $C_5$-$C_{18}$arylalkyl;
$R_2$ is $OR_3$ or $NHR_4$;
$R_3$ and $R_4$ are selected from the group consisting of H, $C_1$-$C_{22}$alkyl, $C_3$-$C_{12}$cycloalkyl, $C_3$-$C_{12}$cycloalkyl interrupted by O and/or $NR_5$, $C_4$-$C_{12}$aryl, and $C_5$-$C_{18}$arylalkyl; and
$R_5$ is H or $C_1$-$C_8$alkyl;
wherein each aryl moiety is unsubstituted or substituted by $C_1$-$C_4$alkyl, $C_1$-$C_4$alkoxy, $C_1$-$C_4$acyl, $C_1$-$C_4$acyloxy, $C_1$-$C_4$acylamino, $CF_3$, OH, or amino; and
wherein the article and/or material is selected from the group consisting of medical device materials, fabrics, paper, nonwovens, wood, and leather.

2. The method of claim 1, wherein each aryl moiety is selected from the group consisting of phenyl, naphthyl, pyridyl, and chinolinyl.

3. The method according to claim 1, wherein
$R_1$ is $C_1$-$C_{12}$alkyl, $C_3$-$C_{12}$cycloalkyl, pyridyl, phenyl, $C_7$-$C_{18}$phenylalkyl;
$R_2$ is $OR_3$ or $NHR_4$; and
$R_3$ and $R_4$ are selected from the group consisting of H, $C_1$-$C_{12}$alkyl, $C_3$-$C_{12}$cycloalkyl, pyridyl, phenyl, and $C_7$-$C_{18}$phenylalkyl.

4. The method according to claim 1, wherein the compound of formula I is applied in an amount 0.01 to 15% by weight, relative to the overall weight of the article and/or material, or in an amount of 0.1 to 100000 mg per square meter of surface treated.

5. A method for achieving an antimicrobial, preservative and/or microorganism adhesion inhibiting effect for protection within an article and/or material or on the surface of an article and/or material, which method comprises:
applying a compound shown in formula II or formula III to the article and/or the material in an amount effective to protect against action of microbes:

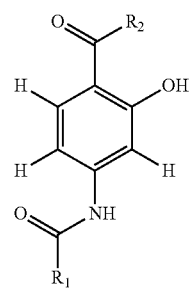

(II)

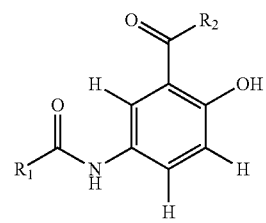

(III)

wherein
$R_1$ is $C_1$-$C_{12}$alkyl, $C_3$-$C_{12}$cycloalkyl, pyridyl, phenyl, $C_7$-$C_{18}$phenylalkyl; and $R_2$ is $OR_3$ or $NHR_4$, $R_3$ and $R_4$ are selected from the group consisting of H, $C_1$-$C_{12}$alkyl, $C_3$-$C_{12}$cycloalkyl, pyridyl, phenyl, and $C_7$-$C_{18}$phenylalkyl; and $R_5$ is H or $C_1$-$C_8$alkyl; and wherein the article and/or material is selected from the group consisting of medical device materials, fabrics, paper, nonwovens, wood, and leather.

6. A method for disaggregation of a microbial biofilm and/or for inhibition of microbial growth of the biofilm-forming microorganisms and/or for killing of microorganisms capable of building a biofilm, the method comprising:

treating a living surface selected from tooth surfaces and oral mucosa or a non-living surface susceptible to biofouling with a compound of formula I or its adduct or salt thereof to protect against action of microbes, wherein the compound of formula I is defined below wherein

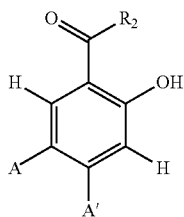
(I)

one of A and A' is a residue of the formula I'

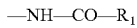
—NH—CO—$R_1$ (I')

while the other is hydrogen;

$R_1$ is $C_1$-$C_{22}$alkyl, $C_3$-$C_{12}$cycloalkyl, $C_3$-$C_{12}$cycloalkyl interrupted by O and/or $NR_5$, $C_4$-$C_{12}$aryl, $C_5$-$C_{18}$arylalkyl;

$R_2$ is $OR_3$ or $NHR_4$;

$R_3$ and $R_4$ are selected from the group consisting of H, $C_1$-$C_{22}$alkyl, $C_3$-$C_{12}$cycloalkyl, $C_3$-$C_{12}$cycloalkyl interrupted by O and/or $NR_5$, $C_4$-$C_{12}$aryl, and $C_5$-$C_{18}$arylalkyl; and $R_5$ is H or $C_1$-$C_8$alkyl;

wherein each aryl moiety is unsubstituted or substituted by $C_1$-$C_4$alkyl, $C_1$-$C_4$alkoxy, $C_1$-$C_4$acyl, $C_1$-$C_4$acyloxy, $C_1$-$C_4$acylamino, $CF_3$, OH, or amino.

7. A method of bactericide or fungicide treatment of tooth surfaces or nails comprising:

applying a compound of formula I or an adduct or salt thereof to the tooth surfaces or nails in an amount effective to protect against action of bacteria or fungi, wherein the compound of formula I is defined below wherein

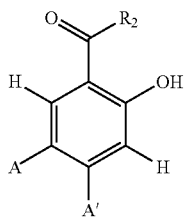
(I)

one of A and A' is a residue of the formula I'

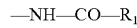
—NH—CO—$R_1$ (I')

while the other is hydrogen;

$R_1$ is $C_1$-$C_{22}$alkyl, $C_3$-$C_{12}$cycloalkyl, $C_3$-$C_{12}$cycloalkyl interrupted by O and/or $NR_5$, $C_4$-$C_{12}$aryl, $C_5$-$C_{18}$arylalkyl;

$R_2$ is $OR_3$ or $NHR_4$;

$R_3$ and $R_4$ are selected from the group consisting of H, $C_1$-$C_{22}$alkyl, $C_3$-$C_{12}$cycloalkyl, $C_3$-$C_{12}$cycloalkyl interrupted by O and/or $NR_5$, $C_4$-$C_{12}$aryl, and $C_5$-$C_{18}$arylalkyl; and $R_5$ is H or $C_1$-$C_8$alkyl;

wherein each aryl moiety is unsubstituted or substituted by $C_1$-$C_4$alkyl, $C_1$-$C_4$alkoxy, $C_1$-$C_4$acyl, $C_1$-$C_4$acyloxy, $C_1$-$C_4$acylamino, $CF_3$, OH, or amino.

8. A method for antimicrobial treatment and/or disinfection of oral mucosa or nails comprising:

applying a compound of formula I or an adduct or salt thereof to the oral mucosa or nails in an amount effective to treat and/or disinfect the oral mucosa or nails, wherein the compound of formula I is an antimicrobial active for treatment of infection of the mucosal membranes or nails, or treatment of injuries of the skin and/or mucosal membranes, and wherein the compound of formula I is defined below wherein

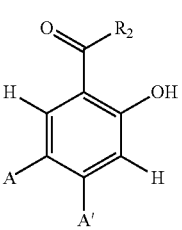
(I)

one of A and A' is a residue of the formula I'

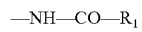
—NH—CO—$R_1$ (I')

while the other is hydrogen;

$R_1$ is $C_1$-$C_{22}$alkyl, $C_3$-$C_{12}$cycloalkyl, $C_3$-$C_{12}$cycloalkyl interrupted by O and/or $NR_5$, $C_4$-$C_{12}$aryl, $C_5$-$C_{18}$arylalkyl;

$R_2$ is $OR_3$ or $NHR_4$;

$R_3$ and $R_4$ are selected from the group consisting of H, $C_1$-$C_{22}$alkyl, $C_3$-$C_{12}$cycloalkyl, $C_3$-$C_{12}$cycloalkyl interrupted by O and/or $NR_5$, $C_4$-$C_{12}$aryl, and $C_5$-$C_{18}$arylalkyl; and $R_5$ is H or $C_1$-$C_8$alkyl;

wherein each aryl moiety is unsubstituted or substituted by $C_1$-$C_4$alkyl, $C_1$-$C_4$alkoxy, $C_1$-$C_4$acyl, $C_{1\text{-}4}$acyloxy, $C_1$-$C_4$acylamino, $CF_3$, OH, or amino.

9. A method for antimicrobial treatment, preservation, deodoration and/or disinfection of inanimate surfaces or inanimate materials the method comprising:

applying a compound of formula I or an adduct or salt thereof to the inanimate surfaces or the inanimate materials selected from the group consisting of medical device surfaces, medical device materials, fabrics, coated surfaces, paper, nonwovens, wood, leather, and metal surfaces, in an amount effective to protect against action of microbes, wherein the compound of formula I is defined below
wherein

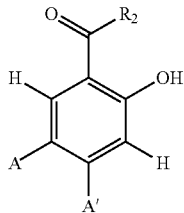

(I)

one of A and A' is a residue of the formula I'

  (I')

while the other is hydrogen;
$R_1$ is $C_1$-$C_{22}$alkyl, $C_3$-$C_{12}$cycloalkyl, $C_3$-$C_{12}$cycloalkyl interrupted by O and/or $NR_5$, $C_4$-$C_{12}$aryl, $C_5$-$C_{18}$arylalkyl;
$R_2$ is $OR_3$ or $NHR_4$;
$R_3$ and $R_4$ are selected from the group consisting of H, $C_1$-$C_{22}$alkyl, $C_3$-$C_{12}$cycloalkyl, $C_3$-$C_{12}$cycloalkyl interrupted by O and/or $NR_5$, $C_4$-$C_{12}$aryl, and $C_5$-$C_{18}$arylalkyl; and
$R_5$ is H or $C_1$-$C_8$alkyl;
wherein each aryl moiety is unsubstituted or substituted by $C_1$-$C_4$alkyl, $C_1$-$C_4$alkoxy, $C_1$-$C_4$acyl, $C_1$-$C_4$acyloxy, $C_1$-$C_4$acylamino, $CF_3$, OH, or amino.

10. A method for deodoration of tooth surfaces or nails comprising:
applying a compound of formula I or an adduct or salt thereof to the tooth surfaces or nails in an amount effective to protect against action of microbes,
wherein the compound of formula I is defined below

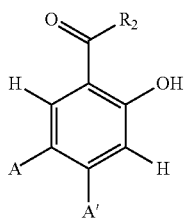

(I)

wherein
one of A and A' is a residue of the formula I'

  (I')

while the other is hydrogen;
$R_1$ is $C_1$-$C_{22}$alkyl, $C_3$-$C_{12}$cycloalkyl, $C_3$-$C_{12}$cycloalkyl interrupted by O and/or $NR_5$, $C_4$-$C_{12}$aryl, $C_5$-$C_{18}$arylalkyl;
$R_2$ is $OR_3$ or $NHR_4$;
$R_3$ and $R_4$ are selected from the group consisting of H, $C_1$-$C_{22}$alkyl, $C_3$-$C_{12}$cycloalkyl, $C_3$-$C_{12}$cycloalkyl interrupted by O and/or $NR_5$, $C_4$-$C_{12}$aryl, and $C_5$-$C_{18}$arylalkyl; and
$R_5$ is H or $C_1$-$C_8$alkyl;
wherein each aryl moiety is unsubstituted or substituted by $C_1$-$C_4$alkyl, $C_1$-$C_4$alkoxy, $C_1$-$C_4$acyl, $C_1$-$C_4$acyloxy, $C_1$-$C_4$acylamino, $CF_3$, OH, or amino.

11. A method for achieving an antimicrobial, preservative and/or microorganism adhesion inhibiting effect for protection within a plastics article and/or on a surface of a plastics article, which method comprises:
incorporating a compound of formula I or an adduct or salt thereof into the material of the plastics article in an amount effective to protect against action of microbes,
wherein

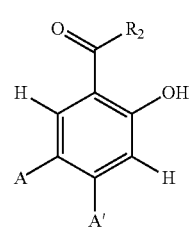

(I)

one of A and A' is a residue of the formula I'

  (I')

while the other is hydrogen;
$R_1$ is $C_1$-$C_{22}$alkyl, $C_3$-$C_{12}$cycloalkyl, $C_3$-$C_{12}$cycloalkyl interrupted by O and/or $NR_5$, $C_4$-$C_{12}$aryl, $C_5$-$C_{18}$arylalkyl;
$R_2$ is $OR_3$ or $NHR_4$;
$R_3$ and $R_4$ are selected from the group consisting of H, $C_1$-$C_{22}$alkyl, $C_3$-$C_{12}$cycloalkyl, $C_3$-$C_{12}$cycloalkyl interrupted by O and/or $NR_5$, $C_4$-$C_{12}$aryl, and $C_5$-$C_{18}$arylalkyl; and
$R_5$ is H or $C_1$-$C_8$alkyl; and
wherein each aryl moiety is unsubstituted or substituted by $C_1$-$C_4$alkyl, $C_1$-$C_4$alkoxy, $C_1$-$C_4$acyl, $C_1$-$C_4$acyloxy, $C_1$-$C_4$acylamino, $CF_3$, OH, or amino.

\* \* \* \* \*